(12) United States Patent
Alex et al.

(10) Patent No.: US 9,428,472 B2
(45) Date of Patent: Aug. 30, 2016

(54) METHODS OF TREATING BACTERIAL INFECTIONS WITH 1,2-BENZISOTHIAZOLINONE AND ISOINDOLINONE DERIVATIVES

(75) Inventors: Deepu Alex, Washington, DC (US); Richard Calderone, Chevy Chase, MD (US); Stephen Peters, Washington, DC (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 14/238,570

(22) PCT Filed: Aug. 16, 2012

(86) PCT No.: PCT/US2012/051123
§ 371 (c)(1),
(2), (4) Date: Jun. 16, 2014

(87) PCT Pub. No.: WO2013/025897
PCT Pub. Date: Feb. 21, 2013

(65) Prior Publication Data
US 2014/0296310 A1    Oct. 2, 2014

Related U.S. Application Data

(60) Provisional application No. 61/524,069, filed on Aug. 16, 2011.

(51) Int. Cl.
*C07D 275/04*    (2006.01)
*A61K 31/428*    (2006.01)

(52) U.S. Cl.
CPC ........... *C07D 275/04* (2013.01); *A61K 31/428* (2013.01)

(58) Field of Classification Search
USPC ....................................................... 514/373
See application file for complete search history.

(56) References Cited

U.S. PATENT DOCUMENTS

| | | | |
|---|---|---|---|
| 3,761,489 | A | 9/1973 | Grivas |
| 4,041,042 | A | 8/1977 | Fabian et al. |
| 4,113,728 | A | 9/1978 | Baggaley |
| 6,667,316 | B1 | 12/2003 | Man et al. |
| 2003/0109559 | A1 | 6/2003 | Gailunas et al. |
| 2005/0069541 | A1 | 3/2005 | Karlik et al. |
| 2007/0219218 | A1 | 9/2007 | Yu et al. |
| 2008/0009532 | A1 | 1/2008 | Wachtler |

FOREIGN PATENT DOCUMENTS

| | | |
|---|---|---|
| GB | 1271054 | 4/1972 |
| PL | 152 486 B1 | 12/1990 |
| WO | 0142216 | 6/2001 |
| WO | 0146183 | 6/2001 |
| WO | 2006020879 | 2/2006 |
| WO | 2006091858 | 8/2006 |
| WO | 2006116713 | 11/2006 |
| WO | 2006117306 | 11/2006 |
| WO | 2008077597 | 7/2008 |
| WO | 2008084240 | 7/2008 |
| WO | 2008099165 | 8/2008 |
| WO | 2008151183 | 12/2008 |
| WO | 2009010478 | 1/2009 |
| WO | 2010039545 | 4/2010 |

OTHER PUBLICATIONS

Xu et al. Haiyang Kexue (2008), 32(5), 62-66.*
Xu et al. Advanced Materials Research vols. 197-198 (2011), pp. 174-177.*
Sharlow et al PLOS Neglected Tropical Diseases (2010) vol. 4(4) e659 pp. 1-8.*
Chemical Abstracts Registry No. 902840-95-3, indexed in the Registry file on STN CAS ONLINE, Aug. 20, 2006.
Chemical Abstracts Registry No. 902871-26-5, indexed in the Registry file on STN CAS ONLINE, Aug. 21, 2006.
U.S. Appl. No. 13/120,602, Non-Final Office Action, issued Mar. 13, 2014, 19 pages.
Aubert et al., "Nouvelle Voie de Synthese d'isoindolones et d'isoquinoleienes par condensation d'iminophosphoranes avec l'ortho-phtalaldehyde: reactions, mecanismes et etude structurale", Canadian Journal of Chemistry, vol. 68, No. 6, Jun. 1, 1990, pp. 842-851.
Breytenbach et al., "Synthesis and Antimicrobial Activity of Some Isoindolin-1-ones Derivatives", Bioorganic and Medicinal Chemistry Letters, vol. 10, 2000, pp. 1629-1631.
Coudron et al., "Use of time-kill methodology to assess antimicrobial combinations against metronidazole-susceptible and metronidazole-resistant strains of H pylon", Antimicrobial Agents and Chemotherapy, vol. 39, No. 12, Dec. 1995, pp. 2641-2644.
Dolle et al., "Solid/Solution-Phase Annulation Reagents: Single-Step Synthesis of Cyclic Amine Derivatives", Angewandte Chemie, International Edition, vol. 44, No. 36, 2005, pp. 5830-5833.
Mahmoud et al., "Synthesis and biological activities of some new 2-(N-heterocyclic carboxamidomethyl thio) benzoxazoles, benthiazoles and benzimidazoles", Part VIII, European Journal of Medicinal Chemistry—Chimica Therapeutica, vol. 16, No. 4, Jul.-Aug. 1981, pp. 383-384.
Mor et al., "Biological Studies on 1,2-benzisothiazole derivatives. V. Antimicrobial properties of N-akanoic, N-arylalkanoic and N-aryloxyalkanoic derivatives of 1,2-benzisothiazolin-3-one: QSAR study and genotoxicity evaluation", Farmaco, Societa Chimica Italiana, Pavia, IT, vol. 51, No. 7, Jan. 1, 1996, pp. 493-501.

(Continued)

*Primary Examiner* — Nyeemah A Grazier
(74) *Attorney, Agent, or Firm* — Kilpatrick Townsend & Stockton, LLP

(57) ABSTRACT

Methods of treating, preventing and ameliorating bacterial infections with 1,2-benzisothiazolinone and isoindolinone derivatives are disclosed. Pharmaceutical compositions containing 1,2-benzisothiazolinone and isoindolinone derivatives are useful for treating bacterial infections caused by drug resistant strains of bacteria, including but not limited to methicillin and vancomycin bacterial organisms.

14 Claims, 4 Drawing Sheets

(56) References Cited

OTHER PUBLICATIONS

Mosmann, "Rapid colorimetric assay for cellular growth and survival: application to proliferation and cytotoxicity assays", J Immunol Methods 65, Dec. 1983, pp. 55-63.

International Patent Application No. PCT/US2012/051123, International Preliminary Report on Patentability, issued Feb. 27, 2014, 5 pages.

International Patent Application No. PCT/US2012/051123, International Search Report & Written Opinion, issued Oct. 15, 2012, 5 pages.

Repetto et al., "Neutral red uptake assay for the estimation of cell viability/cytotoxicity", Nature Protocols, vol. 3, No. 7, 2008, pp. 1125-1131.

Rufer et al., "Neue Acylierte 2-(4-Aminophenyl)-propionsauren als potentielle Antiphlogistica", European Journal of Medicinal Chemistry, vol. 13, No. 2, Mar. 1, 1978, pp. 193-198.

Sahm et al., "In Vitro Susceptibility Studies of Vancomycin-Resistant Enterococcus faecalis", Antimicrobial Agents and Chemotherapy, vol. 33, 1989, pp. 1588-1591.

Schwan et al., "Synthesis of Antifungal 2-Substituted Phthalimidines", Journal of Pharmaceutical Science, vol. 67, No. 1, Jun. 1, 1978, pp. 863-864.

Scott et al., "3,5-Dialkyl-4-(phthalimidomethyl)isoxazoles, pyrazoles, and isothiazoles. Novel antiandrogens", Journal of Medicinal Chemistry, vol. 16, No. 5, Mar. 1, 1973, pp. 512-516.

Slawik, "Aminomethylamide Derivatives of (3-oxo-1, 2-benzisothiazolin-2-yl) acetic acid and 3- (3-oxo-1, 2-benzisothiazolin-2-yl) propionic acid", Pharmazie, vol. 46, No. 11, CA 117:171291, 1992, Abstract.

Canadian Application No. 2,738,314, "Office Action", mailed Jun. 5, 2015, five pages.

U.S. Appl. No. 13/120,602, "Notice of Allowance", mailed Jan. 30, 2015 (17 pages).

U.S. Appl. No. 13/120,602, "Final Office Action", mailed Sep. 15, 2014 (27 pages).

Canadian Patent Application No. 2,738,314, Office Action mailed Feb. 10, 2016, 3 pages.

Australian Application No. 2012296543, "Patent Examination Report No. 1", mailed Aug. 20, 2015, 3 pages.

\* cited by examiner

METHODS OF TREATING BACTERIAL INFECTIONS WITH 1,2-BENZISOTHIAZOLINONE AND ISOINDOLINONE DERIVATIVES

CROSS REFERENCE TO RELATED APPLICATIONS

This application claims the benefit of priority of U.S. Provisional Application No. 61/524,069, filed Aug. 16, 2011.

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

BACKGROUND

There has been a steady increase in the incidence of resistant bacterial infections in the past decade both in hospital and community acquired settings. There is an urgent need to identify novel compounds and/or drug targets that are active against these pathogens. Surprisingly, 1,2-benzisothiazoline and isoindoline compounds first described in WO 2010/039545, filed on 23 Sep. 2009 and incorporated herein by reference, have shown effectiveness in methods of treating, preventing and/ameliorating bacterial infection in subjects in need thereof.

SUMMARY

Methods of treating, preventing and/or ameliorating bacterial infections in a subject using compositions comprising 1,2-benzisothiazoline and isoindoline compounds are disclosed herein. In one aspect of the present invention, the method comprises administering compounds of formula I below:

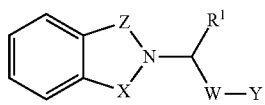

I including pharmaceutically acceptable salts and prodrugs to a subject in need thereof.

For compounds of formula I, $R^1$ is hydrogen or methyl; W is —C(O)NR$^2$—, —C(O)NR$^3$—NR$^4$C(O)—, or substituted or unsubstituted heteroaryl, wherein $R^2$, $R^3$, and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; X is $CH_2$ or S; Y is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl; and Z is C=O or $SO_2$.

In specific embodiments, the method of treatment comprises administering a composition for the treatment of bacterial infections caused by one of more of the organisms selected from the group consisting of *Staphylococcus saprophyticus, Staphylococcus aureus, Micrococcus* sp., *Enterococcus fecalis* and Group A *Streptococcus*.

The method of treatment may further comprise administering a compound or composition described herein, for the treatment of a bacterial infection caused by one or more drug resistant organisms. In a specific embodiment, the drug resistant organism is a methicillin resistant organism. In a specific embodiment, the drug resistant organism is a vancomycin resistant organism.

In certain embodiments, the present invention provides for methods of treating, preventing and/or ameliorating bacterial infections in immunocompromised subjects.

DETAILED DESCRIPTION

Figure 1:
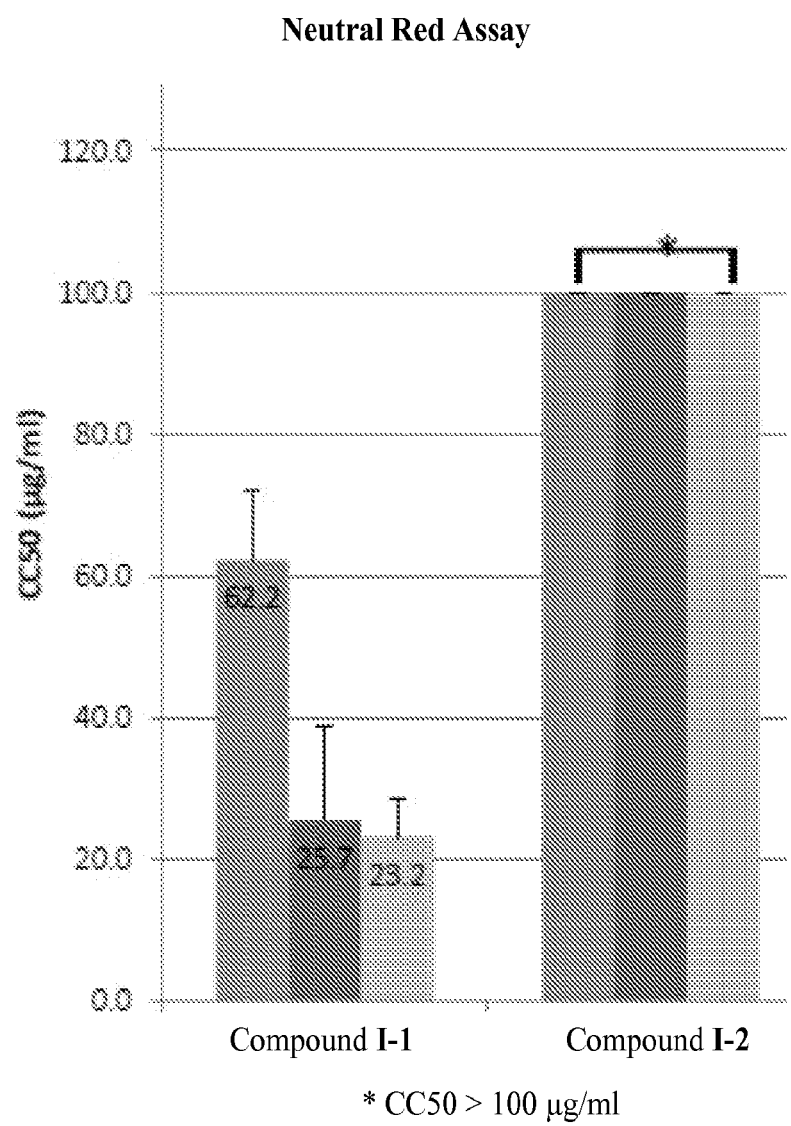
FIG. 1: Neutral red assay cell viability assay determining the toxicity of compounds I-1 and I-2.

The present invention addresses the growing need for therapeutics to treat bacterial infections that are acquired in both community and hospital settings. In particular, the methods described herein have the potential to address the unmet need for therapies that can treat drug resistant strains of bacteria, including, but not limited to methicillin and vancomycin resistant bacterial organisms. Further, the methods described herein may also be useful for treating, preventing and/or ameliorating bacterial infection in subjects that are immune compromised, and thus vulnerable to bacterial infection.

Described herein are methods for treating, preventing and/or ameliorating bacterial infections in a subject by administering compositions comprising 1,2-benzisothiazoline and isoindoline compounds of formulas I-VIII, to subjects in need thereof. Surprisingly, 1,2-benzisothiazoline and isoindoline compounds first described in WO 2010/039545, filed on 23 Sep. 2009 and incorporated herein by reference, have shown effectiveness in the method of treating, preventing and/ameliorating bacterial infection in subjects in need thereof.

In one aspect of the invention, the method of treating preventing and/or ameliorating bacterial infections comprises administering compounds of formula I below:

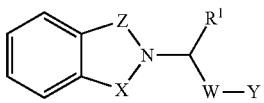

including pharmaceutically acceptable salts or prodrugs to a subject in need thereof.

In formula I, $R^1$ is hydrogen or methyl;

W is —C(O)NR$^2$—, —C(O)NR$^3$—NR$^4$C(O)—, or substituted or unsubstituted heteroaryl, wherein $R^2$, $R^3$, and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl. In certain embodiments, W is —C(O)NH—, —C(O)NCH$_3$—, or —C(O)NH—NHC(O)—. In certain embodiments, W is

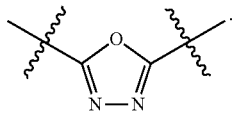

In certain embodiments, W is —C(O)NR$^2$ and $R^2$ is hydrogen or methyl.

Additionally in formula I, X is CH$_2$ or S;

Y is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some embodiments, Y is substituted or unsubstituted benzyl, substituted or unsubstituted aryl, methyl, or amino.

In specific embodiments, the Y group of formula I can have, for example, one of the following Structures A1-A4:

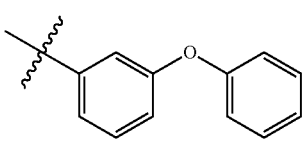

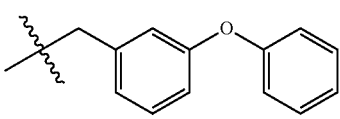

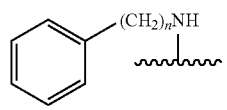

Further in formula I, Z is C=O or SO$_2$.

In some embodiments of formula I, W—Y is —C(O)N(R$^2$)Y—. The —N(R$^2$)Y— group of formula I can have, for example, one of the following Structures B1-B16:

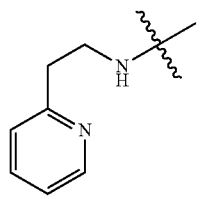

wherein n is 0, 1, or 2.

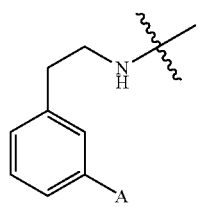

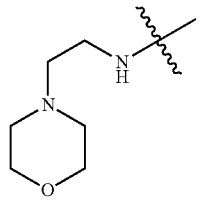

wherein A is F or OCH$_3$.

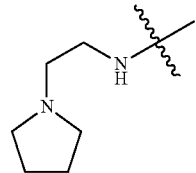

-continued

B6 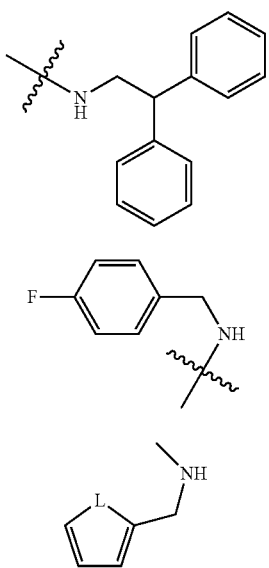

B7

B8 wherein L is O or NH.

B9 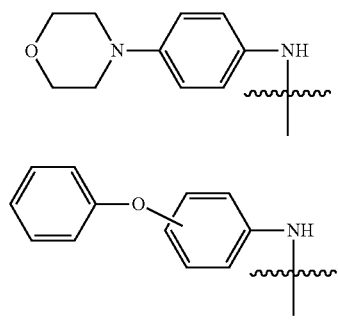

B10

As shown in Structure B10, the phenoxy group can be in the ortho, meta, or para position.

B11 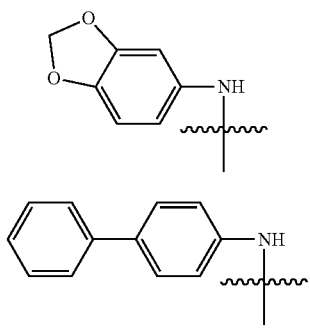

B12

B13 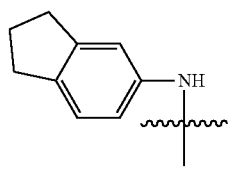

-continued

B14 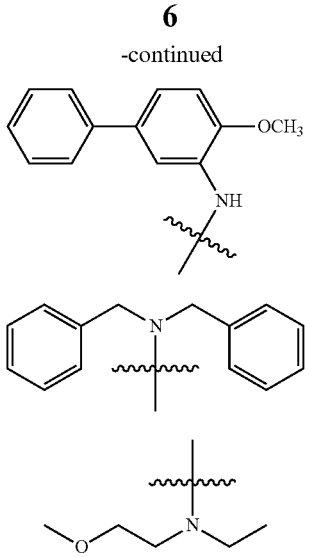

B15

B16

In formula I, when W is —C(O)NR$^2$—, the R$^2$ and Y groups can be combined to form substituted or unsubstituted aryl, substituted or unsubstituted heteroaryl, substituted or unsubstituted cycloalkyl, or substituted or unsubstituted heterocycloalkyl groups. For example, R$^2$ can be a propyl amine group and Y can be an ethyl group that combine to form a piperidine group. Further examples of the —N(R$^2$)Y— group of formula I wherein W—Y is —C(O)N(R$^2$)Y—, and R$^2$ and Y combine are shown in the following Structures B17-B19:

B17 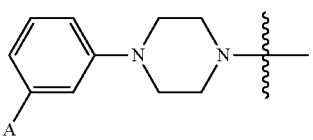

wherein A is H, —OCH$_3$, or CF$_3$.

B18 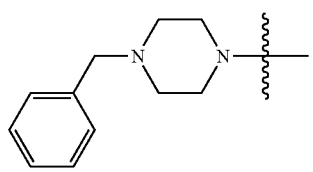

B19 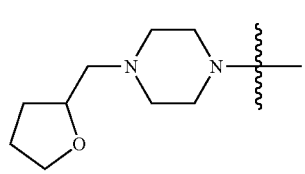

In one example of formula I, when Z is C═O and R$^1$ is methyl, W—Y is not

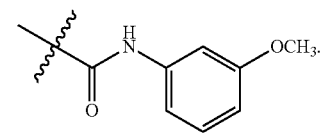 [SMILES: *C(=O)Nc1cccc(OC)c1]

In an additional example of formula I, when Z is C=O, X is S, and R¹ is H, W—Y is not
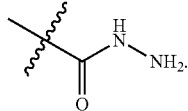 [SMILES: *C(=O)NN]
In a further example of formula I, when Z is C=O, X is S, and R¹ is methyl, W—Y is not
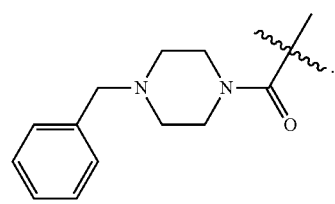 [SMILES: *C(=O)N1CCN(Cc2ccccc2)CC1]
Additional examples of formula I are as follows:
I-1
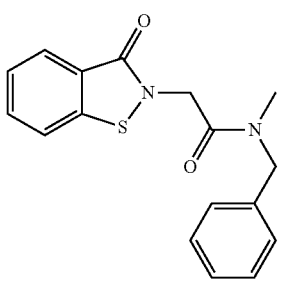
I-2
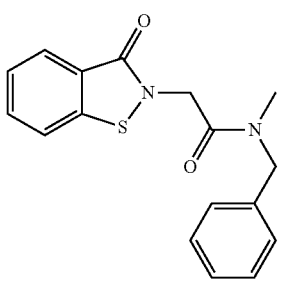
I-3
I-4
I-5
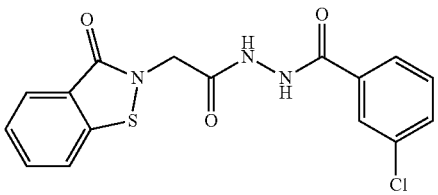
I-6
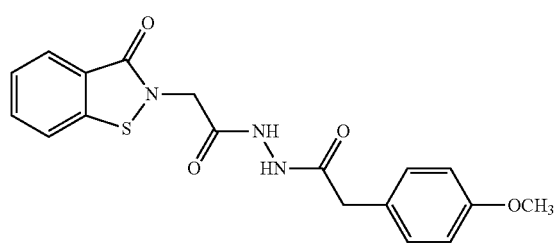
I-7
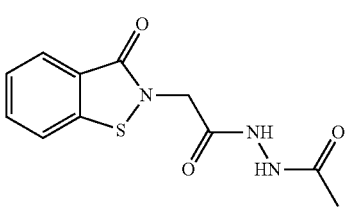
I-8
I-9
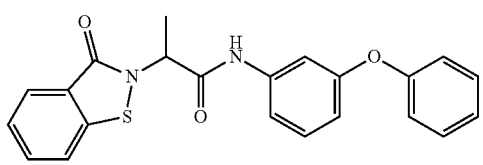
I-10
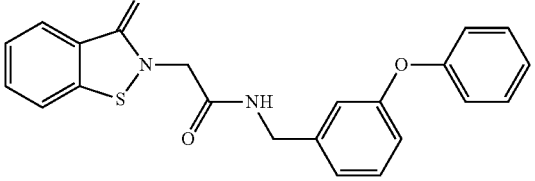
I-11
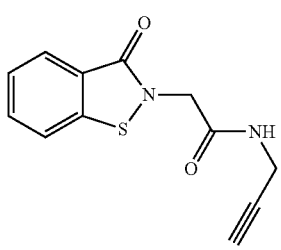

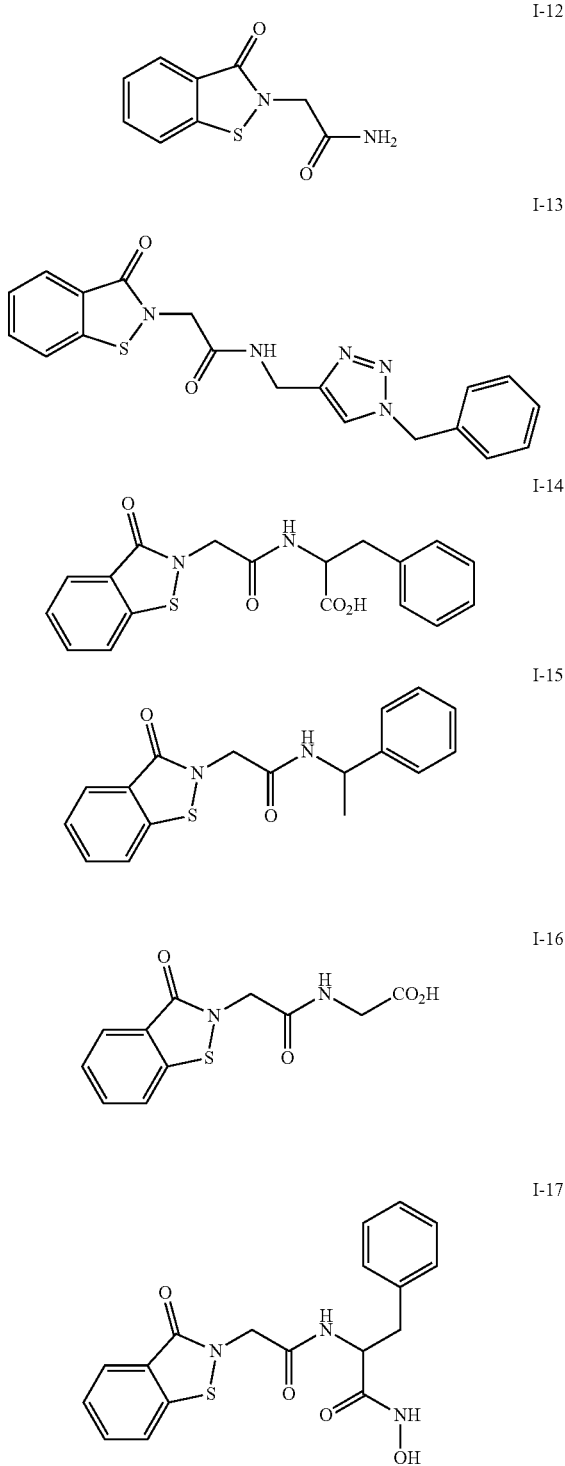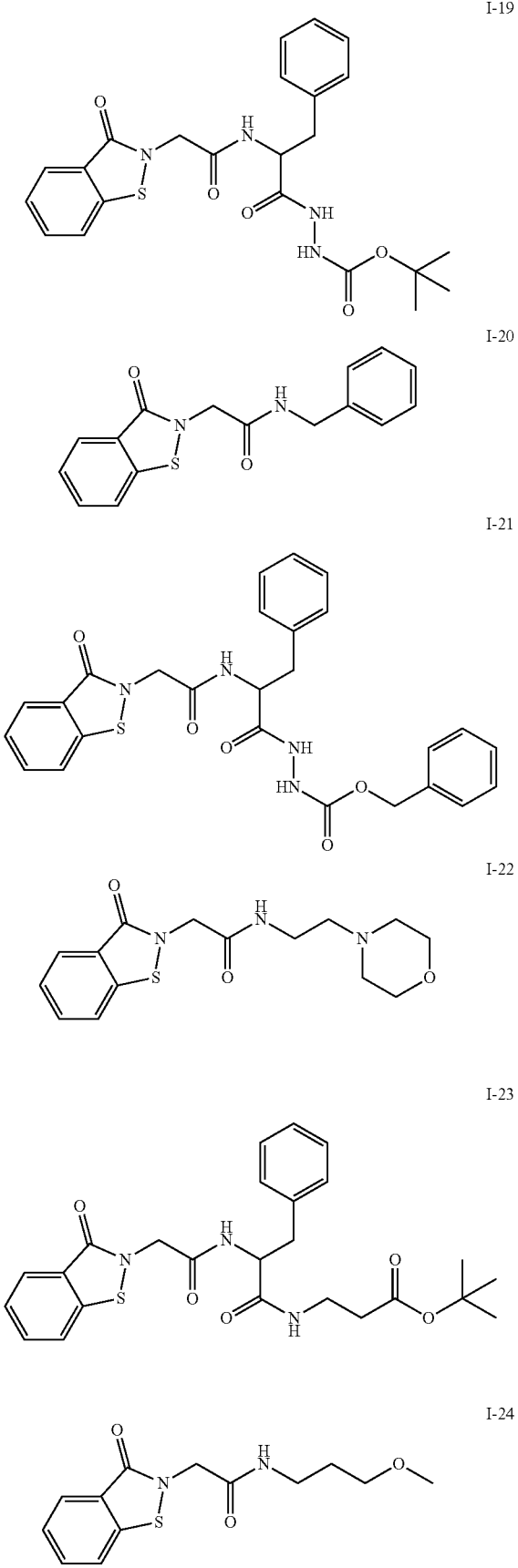

-continued

I-25

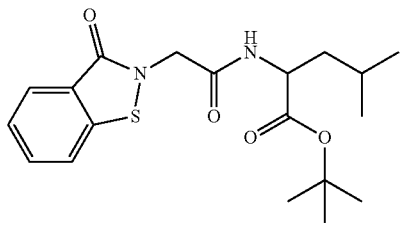

In another aspect of the invention, the method of treating preventing and/or ameliorating bacterial infections comprises administering compounds of formula II below:

II

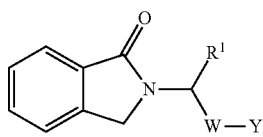

including pharmaceutically acceptable salts or prodrugs to a patient in need thereof.

In formula II, $R^1$ is hydrogen or methyl.

Also in formula II, W is —C(O)NR²—, —C(O)NR³—NR⁴C(O)—, or substituted or unsubstituted heteroaryl, wherein $R^2$, $R^3$, and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl. In some embodiments, W is —C(O)NH—, —C(O)NCH₃—, or —C(O)NH—NHC(O)—. In some embodiments, W is

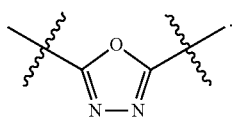

Additionally in formula II, Y is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some embodiments, Y is substituted or unsubstituted benzyl, substituted or unsubstituted aryl, methyl, or amino. The Y group of formula II can have, for example, one of the Structures A1-A4.

In one embodiment of formula II, when $R^1$ is methyl, W—Y is not

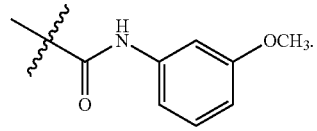 [SMILES: *C(=O)Nc1cccc(OC)c1]

In another aspect of the invention, the method of treating preventing and/or ameliorating bacterial infections comprises administering compounds of formula III below:

III

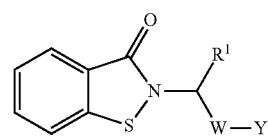

including pharmaceutically acceptable salts or prodrugs to a patient in need thereof.

In formula III, $R^1$ is hydrogen or methyl.

Also in formula III, W is —C(O)NR²—, —C(O)NR³—NR⁴C(O)—, or substituted or unsubstituted heteroaryl, wherein $R^2$, $R^3$, and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl. In some embodiments, W is —C(O)NH—, —C(O)NCH₃—, or —C(O)NH—NHC(O)—. In some embodiments, W is

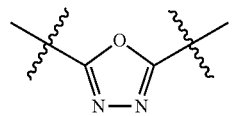

Additionally in formula III, Y is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some embodiments, Y is substituted or unsubstituted benzyl, substituted or unsubstituted aryl, methyl, or amino. The Y group of formula III can have, for example, one of the Structures A1-A4.

In one embodiment of formula III, when $R^1$ is methyl, W—Y is not

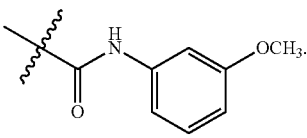 [SMILES: *C(=O)Nc1cccc(OC)c1]

In an additional embodiment of formula III, when $R^1$ is hydrogen, W—Y is not

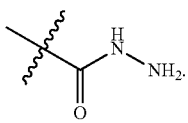

In a further example of formula III, when $R^1$ is methyl, W—Y is not

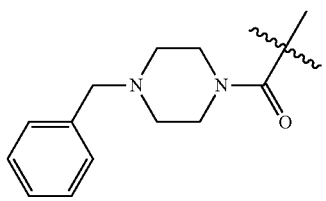

In another aspect of the invention, the method of treating preventing and/or ameliorating bacterial infections comprises administering compounds of formula IV below:

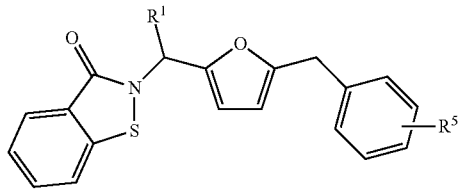

including pharmaceutically acceptable salts or prodrugs to a patient in need thereof.

In formula IV, $R^1$ is hydrogen or methyl. In some examples, $R^1$ is hydrogen.

Also in formula IV, $R^5$ is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some embodiments, $R^5$ is hydrogen or methoxy. In some examples, the $R^5$ group is located in a para position.

In another aspect of the invention, the method of treating preventing and/or ameliorating bacterial infections comprises administering compounds of formula V below:

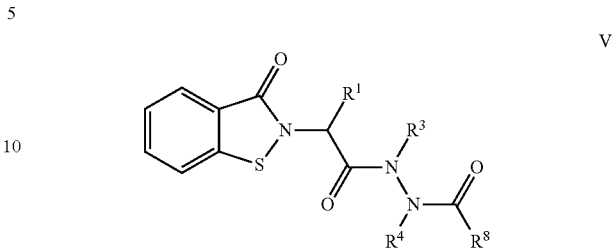

including pharmaceutically acceptable salts or prodrugs to a patient in need thereof.

In formula V, $R^1$ is hydrogen or methyl. In some examples, $R^1$ is hydrogen.

Also in formula V, $R^3$ and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl. In some embodiments, $R^3$ is hydrogen. In some embodiments, $R^4$ is hydrogen.

Additionally in formula V, $R^6$ is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some embodiments, $R^6$ is methyl, benzyl, m-chlorophenyl, or p-methoxybenzyl.

In another aspect of the invention, the method of treating preventing and/or ameliorating bacterial infections comprises administering compounds of formula VI below:

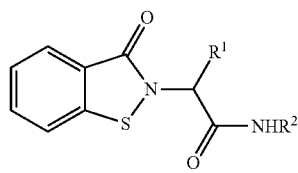

including pharmaceutically acceptable salts or prodrugs to a patient in need thereof.

In formula VI, $R^1$ is hydrogen or methyl. In some examples, $R^1$ is hydrogen.

Also in formula VI, $R^2$ is hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some examples, $R^2$ is a substituted alkyl group. In some examples, $R^2$ is (o-methoxy)phenyl, benzyl, (alpha-methyl)phenyl, N-(2-ethylmorpholine), or (3-methoxy)propyl.

In one embodiment of formula VI, when $R^1$ is methyl, $R^3$ is not

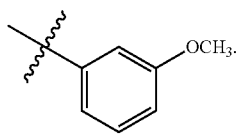 [SMILES: *c1cccc(OC)c1]

In another aspect of the invention, the method of treating preventing and/or ameliorating bacterial infections comprises administering compounds of formula VII below:

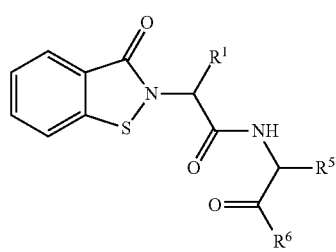

VII including pharmaceutically acceptable salts or prodrugs to a patient in need thereof.

In formula VII, $R^1$ is hydrogen or methyl. In some embodiments, $R^1$ is hydrogen.

Also in formula VII, $R^5$ and $R^6$ are each independently selected from hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl. In some embodiments, $R^5$ is hydrogen, benzyl, or isobutyl. In some embodiments, $R^6$ is hydroxy, —NHOH, —NHNHCO$_2$tBu, —NHNHCO$_2$Bn, or —NH(CH$_2$)$_2$CO$_2$tBu.

In another aspect of the invention, the method of treating preventing and/or ameliorating bacterial infections comprises administering a compound of formula VIII below:

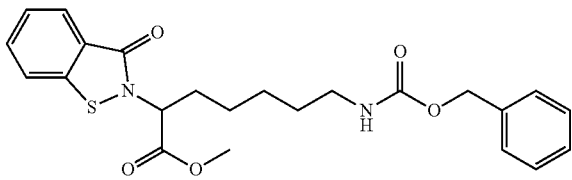 

VIII or pharmaceutically acceptable salts and prodrugs thereof.

As used herein, the terms alkyl, alkenyl, and alkynyl include straight- and branched-chain monovalent substituents. Examples include methyl, ethyl, isobutyl, 3-butynyl, and the like. Heteroalkyl, heteroalkenyl, and heteroalkynyl are similarly defined but may contain O, S, or N heteroatoms or combinations thereof within the backbone. The term cycloalkyl as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term heterocycloalkyl is a type of cycloalkyl group as defined above, and is included within the meaning of the term cycloalkyl, where at least one of the carbon atoms of the ring is replaced with a heteroatom such as, but not limited to, nitrogen, oxygen, sulfur, or phosphorus.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include, furan, pyrrole, thiophene, imidazole, oxazole, pyridine, and pyrazine. Aryl and heteroaryl molecules can also include additional fused rings, for example, benzofuran, indole, benzothiophene, naphthalene, anthracene, and quinoline.

The alkyl, alkenyl, alkynyl, cycloalkyl, aryl, heteroalkyl, heteroalkenyl, heteroalkynyl, heterocycloalkyl, and heteroaryl molecules used herein can be substituted or unsubstituted. As used herein, the term substituted includes the addition of an alkyl, alkenyl, alkynyl, cycloalkyl, aryl, heteroalkyl, heteroalkenyl, heteroalkynyl, heterocycloalkyl, or heteroaryl group (as described herein) to a position attached to the main chain of the alkyl, alkenyl, alkynyl, cycloalkyl, aryl, heteroalkyl, heteroalkenyl, heteroalkynyl, heterocycloalkyl, or heteroaryl, e.g., the replacement of a hydrogen by one of these molecules. Examples of substitution groups include, but are not limited to, hydroxyl, halogen (e.g., F, Br, Cl, or I), and carboxyl groups. Conversely, as used herein, the term unsubstituted indicates the alkyl, alkenyl, alkynyl, cycloalkyl, aryl, heteroalkyl, heteroalkenyl, heteroalkynyl, heterocycloalkyl, or heteroaryl has a full complement of hydrogens, i.e., commensurate with its saturation level, with no substitutions, e.g., linear decane (—(CH$_2$)$_9$—CH$_3$).

The compounds described herein may contain chiral centers. Such chiral centers may be of either the (R) or (S) configuration, or may be a mixture thereof. Thus, the compounds provided herein may be enantiomerically pure, or be stereoisomeric or diastereomeric mixtures. The separation of mixtures of optical isomers to obtain pure enantiomers is well known in the art and is contemplated. Enantiomeric resolution may, for example, be achieved by fractional crystallization of salts with chiral acids or by chromatographic separation on chiral columns.

In the case of amino acid residues, such residues may be of either the L- or D-form. As used herein, the term amino acid refers to α-amino acids which are racemic, or of either the D- or L-configuration. The designation "L" preceding an amino acid designation refers to the L-isomer of the amino acid. The designation "DL" preceding an amino acid designation refers to a mixture of the L- and D-isomers of the amino acid. The chiral centers of the compounds provided herein may undergo epimerization in vivo. As such, the administration of a compound in its (L) form is equivalent, for compounds that undergo epimerization in vivo, to administration of the compound in its (D) form.

The compounds described herein can be prepared in a variety of ways. The compounds can be synthesized using synthetic methods known in the art of synthetic organic chemistry or variations thereon as appreciated by those skilled in the art. The compounds described herein can be prepared from readily available starting materials. Optimum reaction conditions may vary with the particular reactants or solvent used, but such conditions can be determined by one skilled in the art by routine optimization procedures.

Variations on formula I, formula II, formula III, formula IV, formula V, formula VI, formula VII and formula VIII include the addition, subtraction, or movement of the various constituents as described for each compound. Similarly, as described above, when one or more chiral centers is present in a molecule the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4$^{th}$ Ed., Wiley & Sons, 2006, which is incorporated herein by reference in its entirety. The synthesis and subsequent testing of various compounds as described by formula I, formula II, formula III, formula IV, formula V, formula VI, formula VII and formula VIII to determine efficacy is contemplated.

Reactions to produce the compounds described herein can be carried out in solvents which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Examples of compounds described by formula I, wherein X is S, Z is C=O, W is —C(O)NR$^2$, and Y is H; formula III, wherein W is —C(O)NR$^2$, and Y is H; formula VI; or formula VII; and pharmaceutically acceptable salts and prodrugs thereof can be made using the methods shown in Scheme 1. In the synthesis of formula VII, R$^2$ as shown in Scheme 1 is —CH(R$^5$)C(O)R$^6$.

Scheme 1:

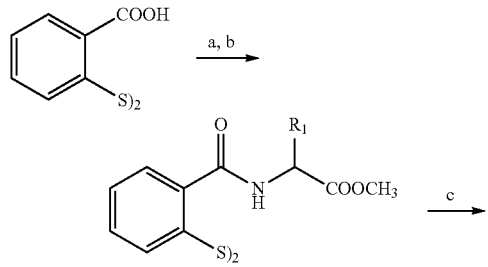

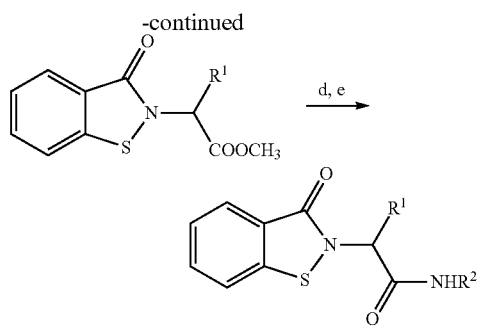

a. SOCl$_2$, reflux; b. (DL)NH$_2$CHR$^1$COOCH$_3$/Et$_3$N
c. Br$_2$/Et$_3$N; d. LiOH, aq. THF; e. EDCI/HOBt, then R$^2$NH$_2$ Examples of compounds described by formula I, wherein X is CH$_2$, Z is C=O, W is —C(O)NR$^2$, and Y is H; or formula II, wherein W is —C(O)NR$^2$, and Y is H; and pharmaceutically acceptable salts and prodrugs thereof can be made using the methods shown in Scheme 2.

Scheme 2:

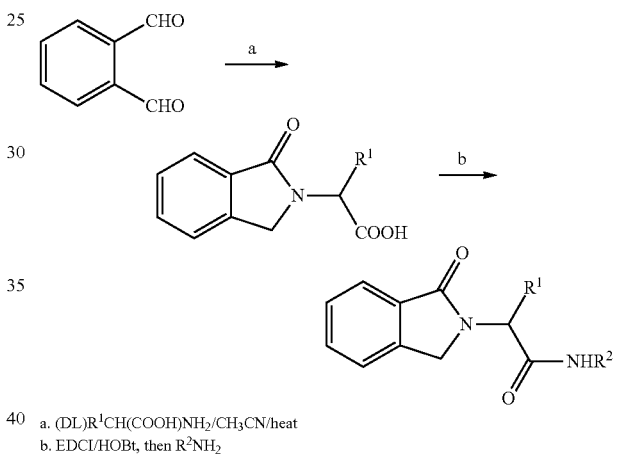

a. (DL)R$^1$CH(COOH)NH$_2$/CH$_3$CN/heat
b. EDCI/HOBt, then R$^2$NH$_2$

Examples of compounds described by formula I, wherein Z is C=O, W is —C(O)NR$^2$, wherein R$^2$ is a substituted triazole, and Y is H and pharmaceutically acceptable salts and prodrugs thereof can be made using the methods shown in Scheme 3. In Scheme 3, T represents a substitution group as described herein.

Scheme 3:

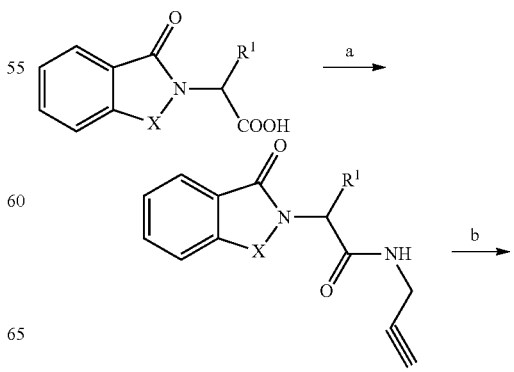

-continued

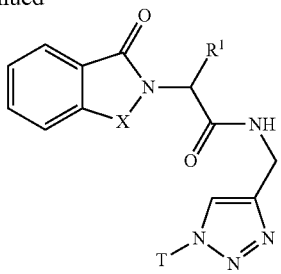

a. EDCI/HOBt, then propargyl amine;
b. T—N₃/CuSO₄/ascorbate/t-BuOH

Examples of compounds described by formula I, wherein Z is C=O, and W is —C(O)NR³—NR⁴C(O)—, wherein R³ and R⁴ are H; formula V; and pharmaceutically acceptable salts and prodrugs thereof can be made using the method shown in Scheme 4.

Scheme 4:

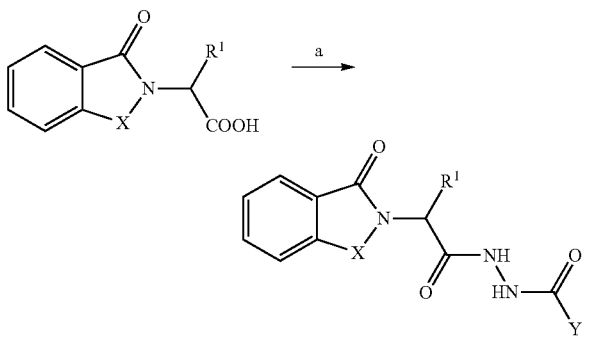

a. EDCI/HOBt, NH₂NHC(=O)Y

Examples of compounds described by formula I, wherein Z is C=O, and W is a substituted or unsubstituted oxadiazole; formula IV; and pharmaceutically acceptable salts and prodrugs thereof can be made using the method shown in Scheme 5.

Scheme 5:

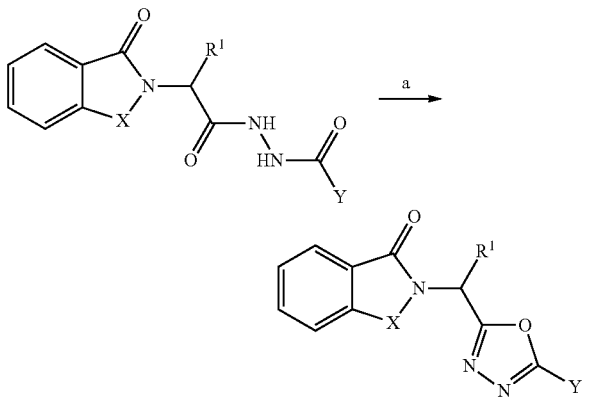

a. p-TsCl/Et₃N

The compounds described herein or pharmaceutically acceptable salts or prodrugs thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include an effective amount of the compounds described herein or a pharmaceutically acceptable salt or prodrug thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected substrate without causing significant undesirable biological effects or interacting in a deleterious manner with any of the other components of the pharmaceutical composition in which it is contained.

In the present invention it was found that the compounds described herein effectively inhibit the activity of bacteria. In an embodiment, it was found that the compounds described herein effectively inhibit the activity of Gram-positive bacterial strains.

Generally, Gram-positive bacteria are bacteria that appear violet (or blue or purple) after Gram-staining by retaining a crystal violet dye in their cell wall during the staining process. The cell wall of Gram-positive bacteria comprises a thick peptidoglycan layer outside their cytoplasmic membrane and has no additional outer membrane. In contrast, Gram-negative bacteria appear pink (or red) after Gram-staining. Their cell wall comprises a thin peptidoglycan layer and an outer membrane.

Gram-positive bacteria comprise, with very few exceptions, the groups of Firmicutes and Actinobacteria (Actinomycetes). Also the terms "Firmicutes" and "Actinobacteria" are well known in the art. As also documented in the appended examples, the compounds and compositions described herein are particularly useful in the inhibition of Gram-positive bacteria. Accordingly, the present invention relates in one embodiment to the medical use of the compounds and compositions described herein in the treatment, prevention and/or amelioration of bacterial infections. In certain embodiments, the compounds and compositions described herein may also be used for the anti-bacterial cleaning of devices and apparatuses.

Gram-positive Firmicutes comprise for example the "Bacilli", including but not limited to the genera *Bacillus, Listeria, Staphylococcus, Enterococcus, Lactobacillus, Lactococcus, Leuconostoc, Pediococcus,* and *Streptococcus,* "Clostridia" (e.g. the genera *Acetobacterium, Clostridium, Eubacterium, Heliobacterium, Heliospirillum, Pectinatus,* and *Sporomusa*) and *Mollicutes* (e.g. genera *Mycoplasma, Spiroplasma, Ureaplasma,* and *Erysipelothrix*). Actinobacteria, include for example the *Actinomyces, Arthrobacter, Corynebacterium, Frankia, Micrococcus, Micromonospora, Nocardia, Propionibacterium, Streptomyces* genera and *Mycobacterium*. Mycobacteria-induced diseases to be treated in accordance with the present invention include, inter alia, tuberculosis, leprosy, tropical skin ulcer, ulceration, abscess, pulmonary disease, granulomatous (skin) disease, opportunistic infections with non-tuberculous mycobacteria as well as diseases elicited by atypical mycobacteria such as *M. avium* including pulmonary disease, lymphadenitis, cutaneous and disseminated diseases, e.g. in immunocompromised patients. The use is not restricted to mycobacteria-induced diseases in humans, but comprises also the use of the present invention in animal diseases, like bovine tuberculosis.

Non-limiting examples of bacterial species which belong to the groups of Firmicutes and Actinobacteria are *Listeria monocytogenes, Listeria welshimeri, Staphylococcus aureus, Staphylococcus epidermidis, Staphylococcus saprophyticus, Staphylococcus lugdunensis, Staphylococcus schleiferi, Staphylococcus caprae, Streptococcus pneumoniae, Streptococcus viridans, Streptococcus pyogenes, Streptococcus agalactiae, Enterococcus faecalis, Enterococcus faecium, Bacillus licheniformis, Bacillus subtilis, Bacillus anthracia, Bacillus cereus, Bacillus thuringiensis, Bacillus larvae, Mycobacterium tuberculosis, Mycobacterium bovis, Mycobacterium leprae, Mycobacterium ulcerans, Mycobacterium kanasasii, Mycobacterium avium, Mycobacterium paratuberculosis, Mycobacterium scrofulaceam, Mycobacterium microti, Mycobacterium africanum, Mycobacterium canettii, Mycobacterium intracellulare, Mycobacterium simiae, Mycobacterium szulgai, Mycobacterium xenopi, Mycobacterium fortuitum, Mycobacterium chelonei, Mycobacterium marinum, Nocardia asteroides,* and *Rhodococcus equi.*

It was also found that the compounds described herein could effectively inhibit the activity of certain drug resistant bacterial organisms. For example, specific multiresistant *Staphylococcus aureus* strains are resistant to known beta-lactam antibiotics (such as methicillin, oxacillin, flucloxacillin) and are accordingly called "Methicillin-Resistant *Staphylococcus aureus* (MRSA)-strains." Only few antibiotics (inter alia, glycopeptides, such as vancomycin or teicoplanin) can be used to treat infections which are caused by MRSA strains. However, some MRSA strains have also become resistant to vancomycin (e.g., vancomycin intermediate *Staphylococcus aureus* (VISA) and vancomycin resistant *Staphylococcus aureus* (VRSA) strains). Also vancomycin resistant Enterococci (VRE), penicillin resistant pneumococci and multiple resistant gram negative bacteria are known in the art.

An advantage of the compounds described herein, is that they may provide a useful method for treating MRSA, VISA, VRSA and/or VRE strains of bacteria. Furthermore, the compositions described herein may be concurrently administered with one or more antibiotic compound to treat bacterial infection in a subject.

In certain embodiments, the present invention provides a method of treating, preventing and/or ameliorating a bacterial infection caused by one or more multiresistant *Staphylococcus aureus* organisms. In certain embodiments, the multiresistant *Staphylococcus aureus* organism is selected from the group consisting of MRSA, VISA, and/or VRSA. In another embodiment, the present invention provides a method for treating, preventing or ameliorating a bacterial infection caused be a VRE and/or a penicillin resistant pneumococci organism. In some embodiments, the present invention provides a method of treating a bacterial infection caused by a Methicillin-Resistant *Staphylococcus aureus* (MRSA) and/or a vancomycin resistant Enterococci (VRE) organism. In a particular embodiment, the drug resistant organism is Methicillin-Resistant *Staphylococcus aureus*. For example, the strain may be Methicillin-Resistant *Staphylococcus aureus* (ATCC 4330). In other embodiments, the drug resistant organism is vancomycin resistant *Enterococcus fecalis*. For example, the strain may be vancomycin resistant *Enterococcus fecalis* (ATCC 51299).

In the context of the present invention, the term "*Enterococcus*" refers to a genus of Gram-positive, lactic acid bacteria of the phylum Firmicutes. The term "pneumococci" used herein refers to bacteria belonging to the Gram-positive species *Streptococcus pneumoniae.*

Some bacteria are also intrinsically resistant (i.e. resistance is not acquired) to antibiotics. For example, Gram-positive *Leuconostoc* and *Pediococcus* species and most *Lactobacillus* species are intrinsically resistant to vancomycin. Accordingly, the methods of the present invention may be particularly useful for the treatment of bacterial infections which are, inter alia, caused by intrinsically resistant bacteria.

The compounds and compositions described herein may also be used for cotherapy. For example, one compound of the present invention or two or more compounds of the invention and one or more antibiotics and/or antiseptics may be employed for the treatment, amelioration or prevention of a bacterial infection. A pharmaceutical composition may comprise the compound(s), antibiotic(s) and/or antiseptic(s). Cotherapy may also include the administration of two or more compounds of the present invention in the absence of further antibiotics or antiseptics. It is also envisaged herein that the compound(s), antibiotic(s) and/or antiseptic(s) might be linked, for example, by formation of conjugates. Accordingly, compound, antibiotics and/or antiseptics may be administered to a subject simultaneously. Of course, a pharmaceutical composition may only comprise the compound(s), while the one or more antibiotics and/or antiseptics are comprised in a different pharmaceutical composition. In that case, it may still be possible to administer the inventive compound(s), antibiotics and/or antiseptics simultaneously; however, the compound(s) may then also be administered before and/or after the one or more antibiotics and/or antiseptics. A person skilled in the art knows how to administer, for example, one or more antibiotics, one or more antiseptics and/or one or more inventive compounds in cotherapy.

Thereby, the one or more antibiotics include, for example, tetracycline-derived antibiotics such as, e.g., tetracycline, doxycycline, chlortetracycline, clomocycline, demeclocycline, lymecycline, meclocycline, metacycline, minocycline, oxytetracycline, penimepicycline, rolitetracycline, or tigecycline; amphenicol-derived antibiotics such as, e.g., chloramphenicol, azidamfenicol, thiamphenicol, or florfenicol; macrolide-derived antibiotics such as, e.g., erythromycin, azithromycin, spiramycin, midecamycin, oleandomycin, roxithromycin, josamycin, troleandomycin, clarithromycin, miocamycin, rokitamycin, dirithromycin, flurithromycin, telithromycin, cethromycin, tulathromycin, carbomycin A, kitasamycin, midecamicine, midecamicine acetate, tylosin (tylocine), or ketolide-derived antibiotics such as, e.g., telithromycin, or cethromycin; lincosamide-derived antibiotics such as, e.g., clindamycin, or lincomycin; streptogramin-derived antibiotics such as, e.g., pristinamycin, or quinupristin/dalfopristin; oxazolidinone-derived antibiotics such as, e.g., linezolid, or cycloserine; aminoglycoside-derived antibiotics such as, e.g., streptomycin, neomycin, framycetin, paromomycin, ribostamycin, kanamycin, amikacin, arbekacin, bekanamycin, dibekacin, tobramycin, spectinomycin, hygromycin B, paromomycin, gentamicin, netilmicin, sisomicin, isepamicin, verdamicin, astromicin, rhodostreptomycin, or apramycin; steroid-derived antibiotics such as, e.g., fusidic acid, or sodium fusidate; glycopeptide-derived antibiotics such as, e.g., vancomycin, oritavancin, telavancin, teicoplanin, dalbavancin, ramoplanin, bleomycin, or decaplanin; beta-lactam-derived antibiotics such as, e.g., amoxicillin, ampicillin, pivampicillin, hetacillin, bacampicillin, metampicillin, talampicillin, epicillin, carbenicillin, carindacillin, ticarcillin, temocillin, azlocillin, piperacillin, mezlocillin, mecillinam, pivmecillinam, sulbenicillin, benzylpenicillin, azidocillin, penamecillin, clometocillin, benzathine benzylpenicillin, procaine benzylpenicillin, phenoxymethylpenicillin, propicillin, benzathine, phenoxymethylpenicillin, pheneticillin, oxacillin, cloxacillin, dicloxacillin, flucloxacillin, meticillin, nafcillin, faropenem, biapenem, doripenem, ertapenem, imipenem, meropenem, panipenem, cefacetrile, cefadroxil, cefalexin, cefaloglycin, cefalonium, cefaloridine, cefalotin, cefapirin, cefatrizine, cefazedone, cefazaflur, cefazolin, cefradine, cefroxadine, ceftezole, cefaclor, cefamandole, cefminox, cefonicid, ceforanide, cefotiam, cefprozil, cefbuperazone, cefuroxime, cefuzonam, cefoxitin, cefotetan, cefmetazole, loracarbef, cefcapene, cefdaloxime, cefdinir, cefditoren, cefetamet, cefixime, cefmenoxime, cefodizime, cefoperazone, cefotaxime, cefpimizole, cefpiramide, cefpodoxime, cefsulodin, ceftazidime, cefteram, ceftibuten, ceftiolene, ceftizoxime, ceftriaxone, flomoxef, latamoxef, cefepime, cefozopran, cefpirome, cefquinome, ceftobiprole, aztreonam, tigemonam, sulbactam, tazobactam, clavulanic acid, ampicillin/sulbactam, sultamicillin, piperacillin/tazobactam, co-amoxiclav, amoxicillin/clavulanic acid, or imipenem/cilastatin; sulfonamide-derived antiobiotics such as, e.g., acetazolamide, benzolamide, bumetanide, celecoxib, chlorthalidone, clopamide, dichlorphenamide, dorzolamide, ethoxzolamide, furosemide, hydrochlorothiazide, indapamide, mafenide, mefruside, metolazone, probenecid, sulfacetamide, sulfadiazine, sulfadimethoxine, sulfadoxine, sulfanilamides, sulfamethoxazole, sulfamethoxypyridazine, sulfasalazine, sultiame, sumatriptan, xipamide, zonisamide, sulfaisodimidine, sulfamethizole, sulfadimidine, sulfapyridine, sulfafurazole, sulfathiazole, sulfathiourea, sulfamoxole, sulfadimethoxine, sulfalene, sulfametomidine, sulfametoxydiazine, sulfaperin, sulfamerazine, sulfaphenazole, or sulfamazone; quinolone-derived antiobiotics such as, e.g., cinoxacin, flumequine, nalidixic acid, oxolinic acid, pipemidic acid, piromidic acid, rosoxacin, ciprofloxacin, enoxacin, fleroxacin, lomefloxacin, nadifloxacin, ofloxacin, norfloxacin, pefloxacin, rufloxacin, balofloxacin, grepafloxacin, levofloxacin, pazufloxacin, sparfloxacin, temafloxacin, tosufloxacin, besifloxacin, clinafloxacin, garenoxacin, gemifloxacin, moxifloxacin, gatifloxacin, sitafloxacin, trovafloxacin, alatrofloxacin, prulifloxacin, danofloxacin, difloxacin, enrofloxacin, ibafloxacin, marbofloxacin, orbifloxacin, pradofloxacin, sarafloxacin, ecinofloxacin, or delafloxacin; imidazole-derived antiobiotics such as, e.g., metronidazole; nitrofuran-derived antiobiotics such as, e.g., nitrofurantoin, or nifurtoinol; aminocoumarin-derived antiobiotics such as, e.g., novobiocin, clorobiocin, or coumermycin A1; ansamycin-derived antiobiotics, including rifamycin-derived antiobiotics such as, e.g., rifampicin (rifampin), rifabutin, rifapentine, or rifaximin; and also further antiobiotics such as, e.g., fosfomycin, bacitracin, colistin, polymyxin B, daptomycin, xibornol, clofoctol, methenamine, mandelic acid, nitroxoline, mupirocin, trimethoprim, brodimoprim, iclaprim, tetroxoprim, or sulfametrole; without being limited thereto.

Furthermore, the one or more antiseptics include, for example, acridine-derived antiseptics such as, e.g., ethacridine lactate, aminoacridine, or euflavine; amidine-derived or biguanide-derived antiseptics such as, e.g., dibrompropamidine, chlorhexidine, propamidine, hexamidine, or polihexanide; phenol-derived antiseptics such as, e.g., phenol, hexachlorophene, policresulen, triclosan, chloroxylenol, or biphenylol; nitrofuran-derived antiseptics such as, e.g., nitrofurazone; iodine-based antiseptics such as, e.g., iodine/octylphenoxypolyglycolether, povidone-iodine, or diiodohydroxypropane; quinoline-derived antiseptics such as, e.g., dequalinium, chlorquinaldol, oxyquinoline, or clioquinol; quaternary ammonium-derived antiseptics such as, e.g., benzalkonium, cetrimonium, cetylpyridinium, cetrimide, benzoxonium chloride, or didecyldimethylammonium chloride; mercurial antiseptics such as, e.g., mercuric amidochloride, phenylmercuric borate, mercuric chloride, mercurochrome, thiomersal, or mercuric iodide; silver-based antiseptics such as, e.g., silver nitrate; alcoholic antiseptics such as, e.g., propanol (including isopropanol), or ethanol; and also further antiseptics such as, e.g., potassium permanganate, sodium hypochlorite, hydrogen peroxide, eosin, tosylchloramide sodium, dichlorobenzyl alcohol, ambazone, benzethonium, myristyl-benzalkonium, hexylresorcinol, or acriflavinium chloride; without being limited thereto.

Cotherapy using inventive compound(s), antibiotic(s) and/or antiseptic(s) may result in a synergistic effect, i.e. the agents acting together may create an effect greater than that predicted by knowing only the separate effects of the individual agents. Such a synergistic effect might be particularly advantageous if less amounts of the compound(s), antibiotic(s) and/or antiseptic(s) may then be used. Thus, possible side-effects of the compound(s), antibiotic(s) and/or antiseptic(s) might be diminished or avoided.

It is known that antibiotics, in particular penicillin and derivatives thereof, may elicit allergic reactions in about 1 out of 7000 patients. The methods of the present invention may thus be advantageous for the treatment of bacterial infections, whereby the subjects to be treated are allergic to antibiotics known in the art.

As a further advantageous property, the present compound is not only useful for the treatment of bacterial or protozoan infections but it is also useful for the elimination or destruction of biofilms. As described herein below in more detail, a biofilm is a complex aggregation (i.e. community) of microorganisms (e.g. bacterial, fungal, algal) enveloped by extracellular biopolymers produced by microbial cells. Biofilms are formed, for example, on surfaces of technical devices such as surgical instruments. The compounds of the present invention are particularly advantageous when such biofilms are to be destroyed but the application of heat, antibiotics known in the art or disinfectants is to be avoided.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (10, Inc.; Bridgewater, N.J.), polyethylene glycol (PEG), and PLURONICS™ (BASF; Florham Park, N.J.).

Compositions containing the compounds described herein or pharmaceutically acceptable salts or prodrugs thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration of the compounds described herein or a pharmaceutically acceptable salt or prodrug thereof include capsules, tablets, pills, powders, and granules. In such solid dosage forms, the compounds described herein or a pharmaceutically acceptable salt or prodrug thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration of the compounds described herein or pharmaceutically acceptable salts or prodrugs thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include adjuvants, such as wetting, emulsifying, suspending, sweetening, flavoring, or perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or pharmaceutically acceptable salts or prodrugs thereof for rectal administrations are preferably suppositories which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or pharmaceutically acceptable salts or prodrugs thereof include ointments, powders, sprays, and inhalants. The compounds described herein or pharmaceutically acceptable salts or prodrugs thereof are admixed under sterile conditions with a physiologically acceptable carrier and any preservatives, buffers, or propellants as may be required. Ophthalmic formulations, ointments, powders, and solutions are also contemplated as being within the scope of the compositions.

The term pharmaceutically acceptable salt as used herein refers to those salts of the compounds described herein that are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See Stahl and Wermuth, Pharmaceutical Salts: Properties, Selection, and Use, Wiley-VCH, 2008, which is incorporated herein by reference in its entirety, at least, for compositions taught therein.)

Immunocompromised subjects include, for example, HIV-positive subjects; subjects undergoing immunotherapy; cancer patients; individuals with viral infections; individuals with an autoimmune disease; patients with malignancies, leukemias, collagen-vascular diseases, or congenital or acquired immunodeficiency; organ-transplant recipients receiving immunosuppressive therapy (e.g., organ transplant recipients); and other patients receiving immunosuppressive therapy. As used herein the term treating or treatment includes prevention; delay in onset; diminution, eradication, or delay in exacerbation of signs or symptoms after onset; and prevention of relapse.

The methods and compounds or compositions as described herein are useful for both prophylactic and therapeutic treatment of bacterial infections. For prophylactic use, a therapeutically effective amount of the compounds or compositions described herein are administered to a subject prior to exposure (e.g., before or when traveling to a location where bacterial infections are possible), during a period of potential exposure to bacterial infections, or after a period of potential exposure to bacterial infections. Prophylactic administration can occur for several days to weeks prior to potential exposure, during a period of potential exposure, and for a period of time, e.g., several days to weeks, after potential exposure. Therapeutic treatment involves administering to a subject a therapeutically effective amount of the compounds or compositions described herein after a bacterial infection is diagnosed.

Administration of compounds or compositions described herein or pharmaceutically acceptable salts or prodrugs thereof can be carried out using therapeutically effective amounts of the compounds or compositions described herein or pharmaceutically acceptable salts or prodrugs thereof for periods of time effective to treat bacterial infections. The effective amount of the compounds or compositions described herein or pharmaceutically acceptable salts or prodrugs thereof may be determined by one of ordinary skill in the art, and includes exemplary dosage amounts for a mammal of from about 0.05 to about 100 mg/kg of body weight of active compound per day, which may be administered in a single dose or in the form of individual divided doses, such as from 1 to 4 times per day. Alternatively, the dosage amount can be from about 0.05 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

The one or more additional agents and the compounds or compositions described herein or a pharmaceutically acceptable salt or prodrug thereof can be administered in any order, including simultaneous administration, as well as temporally spaced order of up to several days apart. The methods may also include more than a single administration of the one or more additional agents and/or the compounds or compositions described herein or a pharmaceutically acceptable salt or prodrug thereof. The administration of the one or more additional agent and the compounds or compositions described herein or a pharmaceutically acceptable salt or prodrug thereof may be by the same or different routes and concurrently or sequentially.

The examples below are intended to further illustrate certain aspects of the methods, compounds, and compositions described herein, and are not intended to limit the scope of the claims.

EXAMPLES

The activity of compounds I-1 and I-2 against *Staphylococcus saprophyticus, Staphylococcus aureus, Micrococcus* sp., *Enterococcus fecalis* and Group A *Streptococcus* was confirmed by broth microdilution method in accordance with CLSI guidelines MO7-A08 and the MIC-50 concentrations were found to be in the range of 1-15 µg/ml. The in vitro toxicity of these compounds was determined by the neutral red (both compounds I-1 and I-2) and MTT (3-(4,5-Dimethylthiazol-2-yl)-2,5-diphenyltetrazolium bromide) assay (compound I-1) in human hepatic cell lines Huh7 and HepG2. Minimal in vitro toxicity was found in both cell lines.

Example 1

Activity Assays for Compounds I-1 and I-2

Broth Microdilution Method:

96 well plates were used to determine the MIC-50 endpoints for most fastidious organisms. The tested compounds were diluted in RPMI to 50 microgram/ml and 0.1 ml was added to the first well. Two-fold dilutions were made in subsequent wells in RPMI to get a range of concentrations from 0.1-50 µg/ml. The volume of diluted compound in each well was 100 microliter. Bacteria were grown in Mueller-Hinton Broth from a single colony from a fresh plate of the tested organism. The broth was grown overnight to 0.5 McFarland standard (108 cells) and further diluted in RPMI to get a final inoculum concentration of 5×105 CFU/mL. 15 minutes after the inoculum had been standardized as described above, 5 µl of this suspension was inoculated to each well containing 0.1 ml of the tested compound. This plate was then kept at 35° C. for 16-20 h in an ambient air incubator. The MIC is the lowest concentration of the tested agent that completely inhibits growth of the organism in the wells. The concentration of inoculum suspension was confirmed by replating on to agar plates. A positive control well with no compound (100 µl of RPMI only with 5 µl of inoculum suspension) and a negative control with no organism (100 µl of compound suspension with 5 µl of RPMI only) were also run. The endpoints of standardized drugs are also determined simultaneously and were compared to those mentioned in CLSI M07-08.

In the course of our screening for antibacterial compounds following the guidelines in CSLI document M02-A10 (disc diffusion method), compound I-1 and I-2 were found to show antibiotic activity against Gram-positive bacterial organisms.

Compound I-1 showed activity against the following organisms: *Staphylococcus saprophyticus, Staphylococcus aureus, Micrococcus* sp., *Enterococcus fecalis* and Group A *Streptococcus*.

In the course of our screening for antibacterial compounds following the guidelines in CSLI document M02-A10 (disc diffusion method), compound I-1 was found to show antibiotic activity against Gram-positive bacterial organisms.

Compound I-2 showed activity against the following organisms: *Staphylococcus saprophyticus, Staphylococcus aureus, Micrococcus* sp., *Enterococcus fecalis* and Group A *Streptococcus*.

In the course of our screening for antibacterial compounds following the guidelines in CSLI document M02-A10 (disc diffusion method), compound I-2 was found to show antibiotic activity against Gram-positive bacterial organisms.

Compounds I-1 and I-2 were also found to exhibit activity against methicillin resistant strains of bacteria. Specifically, compounds I-1 and I-2 were active against *Staphylococcus aureus* ATCC 43300, which is a Methicillin resistant strain of *S. aureus* (MRSA) and *Enterococcus fecalis* ATCC 51299, which is a Vancomycin resistant strain of *E. fecalis* (VRE).

Disc-Diffusion Method

An inoculum of the tested organism was made from an 18-24 h agar plate and was grown overnight to 0.5 McFarland standard. This suspension was then spread on a fresh Mueller-Hinton plate in the following manner: Optimally, within 15 minutes after adjusting the turbidity of the inoculum suspension, a sterile cotton swab was dipped the suspension. The swab was rotated several times and pressed firmly on the inside wall of the tube to remove excess inoculum. The dried surface of the Mueller-Hinton agar plate was then inoculated by streaking the swab over the entire sterile agar surface. Discs of sterile filter paper were inoculated with standard amounts of compounds (5, 10 and 25 microgram) and were dried before application on to the streaked plate. A control disc with the same DMSO % as the test discs were also applied to the plate. The plates were inverted after 15 minutes and were placed in an incubator set to 35° C. After 16-18 h, the plates were examined. The circular zones of inhibition were evaluated by measuring the diameter of the circular margin with no obvious visible growth. The inhibition diameters of standardized drugs against the tested organism were also determined simultaneously and are compared to those mentioned in CLSI M02-A10.

The results for compound I-1 are presented in Table 1 below:

TABLE 1

Disc Inhibition Testing of Compound I-1

| Strain | Conc. (in µg) | Zone diameter |
|---|---|---|
| Staphyloccus saprophyticus | 10 | 18 mm |
| | 25 | 19 mm |
| | 50 | 24 mm |
| Staphylococcus aureus 25923 | 10 | 19 mm |
| | 25 | 20 mm |
| | 50 | 22 mm |
| Staphylococcus aureus 43300 (MRSA) | 10 | 10 mm |
| | 25 | 18 mm |
| | 50 | 20 mm |

TABLE 1-continued

Disc Inhibition Testing of Compound I-1

| Strain | Conc. (in µg) | Zone diameter |
|---|---|---|
| Staphylococcus aureus 29213 | 10 | 19 mm |
| | 25 | 19 mm |
| | 50 | 19 mm |
| Micrococcus sp | 10 | 33 mm |
| | 25 | 34 mm |
| | 50 | 35 mm |
| Enterococcus fecalis 29212 | 10 | 13 mm |
| | 25 | 18 mm |
| | 50 | 21 mm |
| Enterococcus fecalis 51299 (VRE) | 10 | 15 mm |
| | 25 | 20 mm |
| | 50 | 22 mm |
| Group A Streptococci | 10 | 22 mm |
| | 25 | 24 mm |
| | 50 | 25 mm |
| Streptococcus pneumoniae | 10/25/50 | NOT ACTIVE |
| Pseudomonas aeroginosa | 10/25/50 | NOT ACTIVE |
| Shigella sp | 10/25/50 | NOT ACTIVE |
| Klebsiella oxytoca | 10/25/50 | NOT ACTIVE |
| Klebsiella pnemonia 1705 | 10/25/50 | NOT ACTIVE |
| E. Coli 25922 | 10/25/50 | NOT ACTIVE |
| Aeromonas sp | 10/25/50 | NOT ACTIVE |
| Proteus sp 35651 | 10/25/50 | NOT ACTIVE |

The results for compound I-2 are presented in Table 2 below:

TABLE 2

Disc Inhibition Testing of Compound I-2

| Strain | Conc. (in µg) | Zone diameter |
|---|---|---|
| Staphyloccus saprophyticus | 10 | 22 mm |
| | 25 | 24 mm |
| | 50 | 25 mm |
| Staphylococcus aureus 25923 | 10 | 18 mm |
| | 25 | 21 mm |
| | 50 | 23 mm |
| Staphylococcus aureus 43300 (MRSA) | 10 | 19 mm |
| | 25 | 19 mm |
| | 50 | 23 mm |
| Staphylococcus aureus 29213 | 10 | 16 mm |
| | 25 | 18 mm |
| | 50 | 22 mm |
| Micrococcus sp | 10 | 27 mm |
| | 25 | 28 mm |
| | 50 | 29 mm |
| Enterococcus fecalis 29212 | 10 | 14 mm |
| | 25 | 16 mm |
| | 50 | 18 mm |
| Enterococcus fecalis 51299 (VRE) | 10 | 17 mm |
| | 25 | 22 mm |
| | 50 | 24 mm |
| Group A Streptococci | 10 | 20 mm |
| | 25 | 24 mm |
| | 50 | 27 mm |
| Streptococcus pneumoniae | 10/25/50 | NOT ACTIVE |
| Pseudomonas aeroginosa | 10/25/50 | NOT ACTIVE |
| Shigella sp | 10/25/50 | NOT ACTIVE |
| Klebsiella oxytoca | 10/25/50 | NOT ACTIVE |
| Klebsiella pnemonia 1705 | 10/25/50 | NOT ACTIVE |
| E. Coli 25922 | 10/25/50 | NOT ACTIVE |
| Aeromonas sp | 10/25/50 | NOT ACTIVE |
| Proteus sp 35651 | 10/25/50 | NOT ACTIVE |

MBC Determination:

The in vitro bactericidal activities (MBC) were determined by subculturing 10 ul from each microtiter plate well that showed complete inhibition in the MIC experiment, on blood-agar plates. The plates were incubated at 37° C. for 24 h. The MBC was determined to be the lowest drug concentration that resulted either in no growth or in fewer than five colonies.

The MIC-50 values for compounds I-1 and I-2 against the tested gram positive pathogens range from 1-15 ug/ml have been determined. The MBC values for the tested strains are less than or equal to 4 times the MIC-50 values, thereby showing that both compounds exhibit bactericidal activity against the tested organisms. These results are shown in table 3 (compound I-1) and table 4 (compound I-2), below.

TABLE 3

MIC-50 and MBC Against Selected Bacterial Strains for Compound I-1

| Strain | MIC-50 (in µg/ml) | MBC (in µg/ml) |
|---|---|---|
| Staphylocccus saprophyticus | 6.4 | 25.0 |
| Staphylococcus aureus (ATCC 25923) | 3.2 | 6.4 |
| Staphylococcus aureus (ATCC 29213) | 3.2 | 12.5 |
| Staphylococcus aureus (ATCC 43300) (MRSA) | 6.4 | 25.0 |
| Micrococcus sp | 1.6 | 3.2 |
| Enterococcus fecalis (ATCC 29212) | 12.5 | 25.0 |
| Enterococcus fecalis (ATCC 51299) (VRE) | 6.4 | 12.5 |
| Streptococcus pyogenes | 1.6 | 6.4 |

TABLE 3

MIC-50 and MBC Against Selected Bacterial Strains for Compound I-1

| Strain | MIC-50 (in µg/ml) | MBC (in µg/ml) |
|---|---|---|
| Staphylocccus saprophyticus | 3.2 | 12.5 |
| Staphylococcus aureus (ATCC 25923) | 6.4 | 12.5 |
| Staphylococcus aureus (ATCC 29213) | 3.2 | 6.4 |
| Staphylococcus aureus (ATCC 43300) (MRSA) | 3.2 | 12.5 |
| Micrococcus sp | 0.8 | 3.2 |
| Enterococcus fecalis (ATCC 29212) | 6.4 | 12.5 |
| Enterococcus fecalis (ATCC 51299) (VRE) | 6.4 | 12.5 |
| Streptococcus pyogenes | 1.6 | 6.4 |

Example 2

Toxicity Assays

The neutral red cell viability assay and the MTT assays were conducted with the active compounds at defined concentrations in human hepatoma cell lines, Huh7 and HepG2, as described by Repetto et al (Repetto G, Peso A. D. & Zurita J. L., *Neutral red uptake assay for the estimation of cell viability/cytotoxicity*, Nature Protocols 3, 1125-1131 (2008)) and Mosmann et al (Mosmann T., *Rapid colorimetric assay for cellular growth and survival: application to proliferation and cytotoxicity assays*, Journal of Immunological Methods 65 (1-2): 55-63, (December 1983)) respectively. The cell cytotoxicity (CC-50) concentrations were calculated for the HepG2 cell line.

The cell cytotoxicity or CC-50 values for I-1 against human hepatoma cell lines (HepG2 and Huh7) were found to be up to 10 times the MIC-50 concentration at 24 h. Compound I-2 showed no toxicity up to a concentration of 100 microgram/ml. Lower CC-50 values were noted at 48 and 72 hours.

Figure 2:
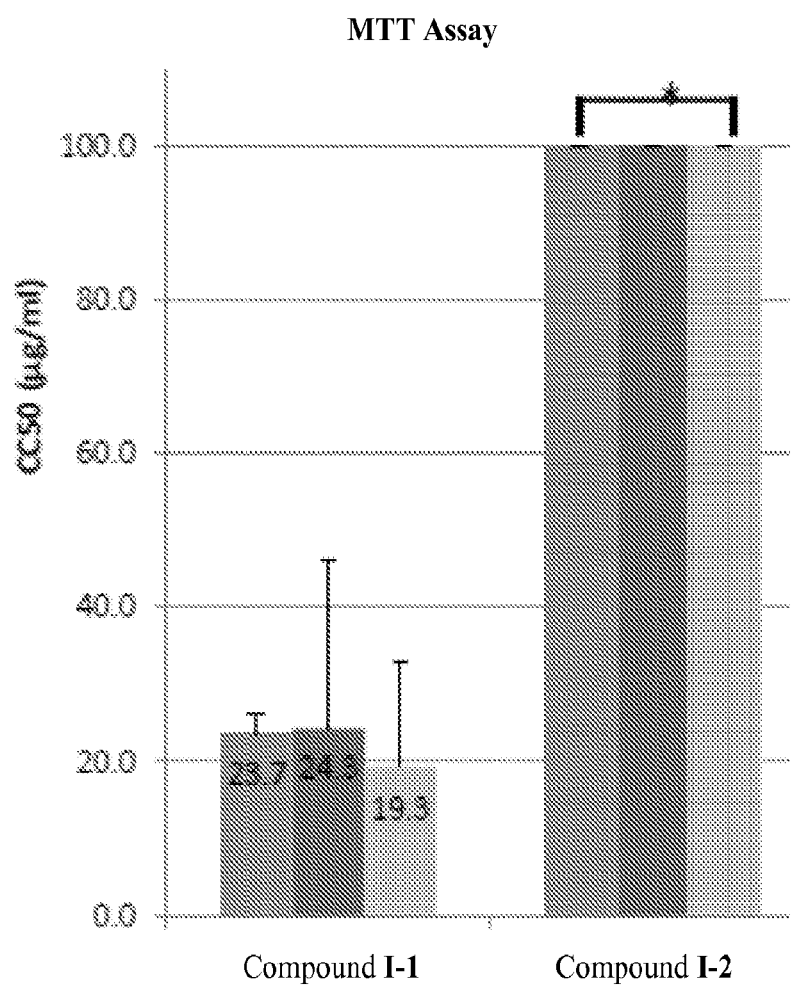
FIG. 2: MTT toxicity assay for compounds I-1 and I-2.

The results of the Neutral Red Assay for compounds I-1 and I-2 may be found in FIG. 1. The results of the MTT Assay for compounds I-1 and I-2 may be found in FIG. 2.

Example 3

Time-Kill Studies for Resistant Pathogens with Compound I-1

Strains at log growth phase were used to prepare suspensions of 5×105 CFUs/ml in 10 ml of RPMI and defined concentrations of the active compounds were added. 100 ul of samples were taken at defined time-periods and the samples were re-plated and incubated for 24 h at 37° C. The viable cell concentration was calculated from the number of CFUs after 24 h. See Coudron, P. E. & Stratton C. W., *Use of time-kill methodology to assess antimicrobial combinations against metronidazole-susceptible and metronidazole-resistant strains of H. pylori*, Antimicrob. Agents Chemother. 39, 2641-44 (December 1995).

Figure 3:
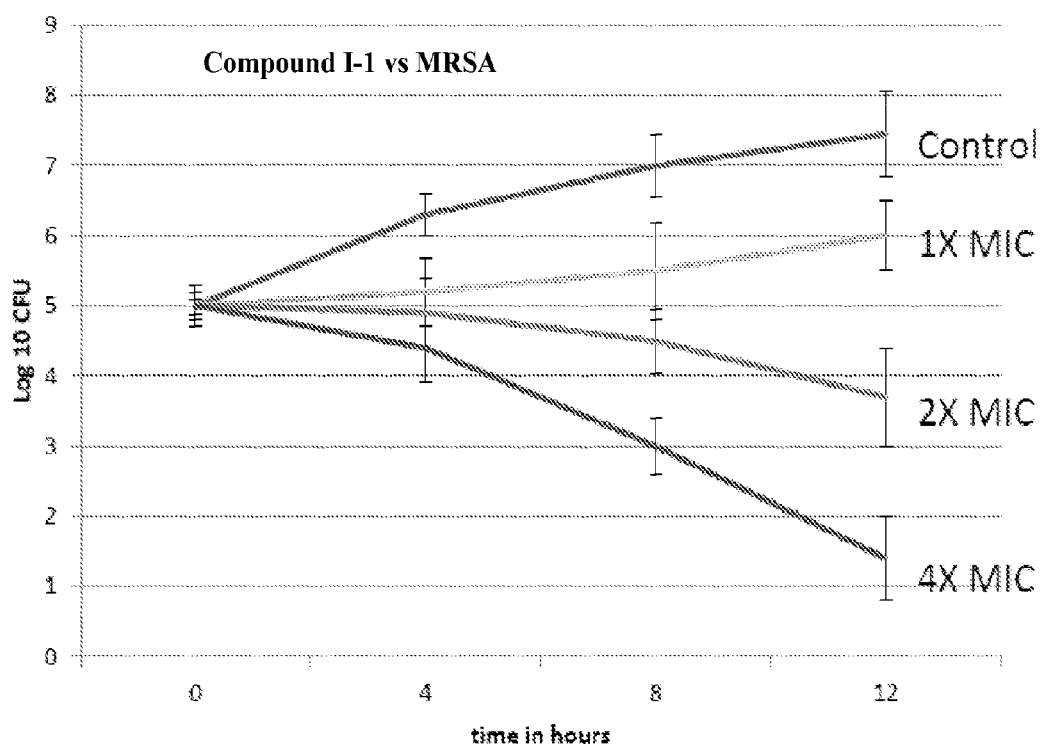
FIG. 3: Time-kill study for the MRSA strain with compound I-1.
Figure 4:
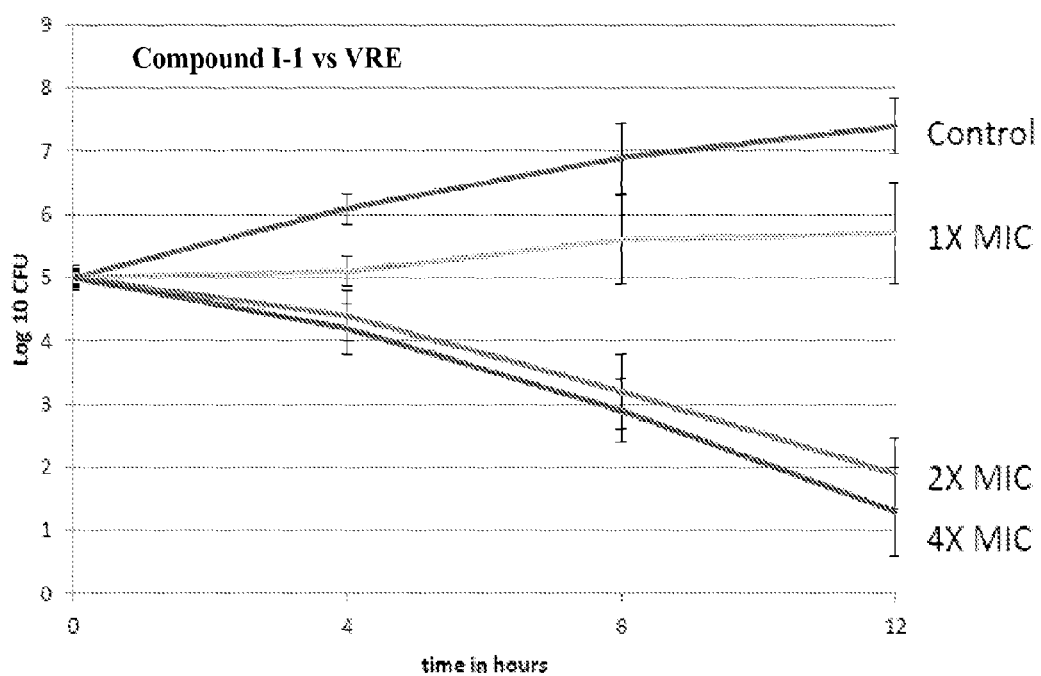
FIG. 4: Time-kill study for the VRE strain with compound I-1.

A reduction of 3 logs in viable organisms for the MRSA strain on treatment with compound I-1 at 4×MIC concentration at 12 h was observed (FIG. 3). A similar reduction was seen with the VRE strain at 2×MIC concentration of compound I-1 (FIG. 4).

What is claimed is:

1. A method of treating a bacterial infection in a subject, wherein a composition comprising a compound of the following formula:

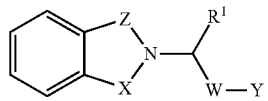

or a pharmaceutically acceptable salt or prodrug, is administered to the subject, wherein:
$R^1$ is hydrogen or methyl;
W is —C(O)NR$^2$— or —C(O)NR$^3$—NR$^4$C(O)—, wherein $R^2$, $R^3$, and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl;
X is $CH_2$ or S;
Y is hydrogen, hydroxy, alkoxy, substituted or unsubstituted amino, substituted or unsubstituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl; and Z is C=O or SO$_2$.

2. A method of treating a bacterial infection to a subject, wherein a composition comprising a compound of the following formula:

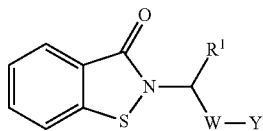

or a pharmaceutically acceptable salt or prodrug, is administered to the subject, wherein:
R$^1$ is hydrogen or methyl;
W is —C(O)NR$^2$— or —C(O)NR$^3$—NR$^4$C(O)—, wherein R$^2$, R$^3$, and R$^4$ are each independently selected from hydrogen, substituted or unsubstituted C$_{1-12}$ alkyl, substituted or unsubstituted C$_{1-12}$ haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and
Y is hydrogen, hydroxy, alkoxy, substituted or unsubstituted amino, substituted or unsubstituted thio, substituted or unsubstituted C$_{1-12}$ alkyl, substituted or unsubstituted C$_{1-12}$ haloalkyl, substituted or unsubstituted C$_{2-12}$ alkenyl, substituted or unsubstituted C$_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

3. A method of treating a bacterial infection in a subject, wherein a composition comprising a compound of the following formula:

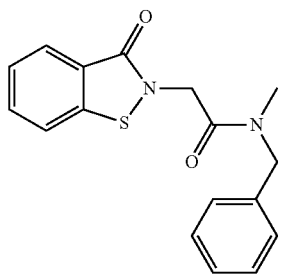 [SMILES: CN(Cc1ccccc1)C(=O)Cn1sc2ccccc2c1=O]

or a pharmaceutically acceptable salt or prodrug is administered to the subject.

4. The method of claim 1, wherein the subject is an immunocompromised subject.

5. The method of claim 1, wherein the bacterial infection being treated is caused by one of more Gram-positive organisms.

6. The method of claim 5, wherein the bacterial infection is caused by one or more bacterial organisms that belong to genera selected from the group consisting of *Staphylococci, Enterrococci, Bacilli* and *Actinobacteria*.

7. The method of claim 6, wherein the bacterial infection is caused by one or more bacterial organisms selected from the group consisting of *Staphylococcus saprophyticus, Staphylococcus aureus, Micrococcus* sp., *Enterococcus fecalis* and Group A *Streptococcus*.

8. The method of claim 5, wherein the bacterial organism is an organism resistant to one or more beta-lactam antibiotics, vancomycin, or both one or more beta-lactam antibiotics and vancomycin.

9. The method of claim 8, wherein the bacterial organism is *Staphylococcus aureus*.

10. The method of claim 8, wherein the bacterial organism is *Enterococcus fecalis*.

11. The method of claim 1, wherein the compound is

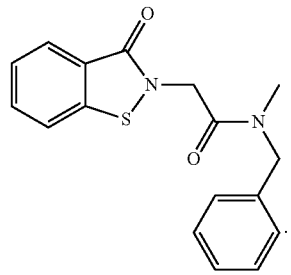 [SMILES: CN(Cc1ccccc1)C(=O)Cn1sc2ccccc2c1=O]

12. The method of claim 1, wherein the compound is

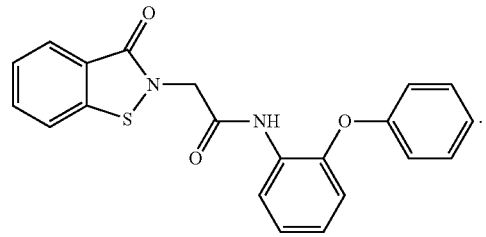 [SMILES: O=C(Cn1sc2ccccc2c1=O)Nc1ccccc1Oc1ccccc1]

13. A method of treating a bacterial infection in a subject, wherein a composition comprising a compound of the following formula:

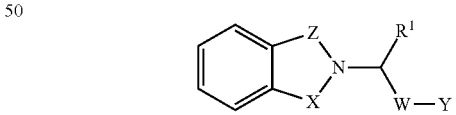

or a pharmaceutically acceptable salt or prodrug, is administered to the subject, wherein:
R$^1$ is hydrogen or methyl;
W is —C(O)NR$^2$—, —C(O)NR$^3$—NR$^4$C(O)—, or

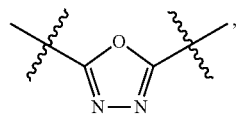

wherein $R^2$, $R^3$, and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl;

X is $CH_2$ or S;

Y is hydrogen, hydroxy, alkoxy, substituted or unsubstituted amino, substituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl; and Z is C=O or $SO_2$.

14. A method of treating a bacterial infection in a subject, wherein a composition comprising a compound of the following formula:

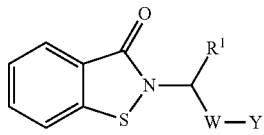

or a pharmaceutically acceptable salt or prodrug, is administered to the subject, wherein:

$R^1$ is hydrogen or methyl;

W is —C(O)$NR^2$—, —C(O)$NR^3$—$NR^4$C(O)—, or

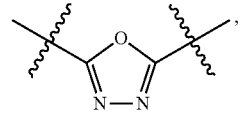

wherein $R^2$, $R^3$, and $R^4$ are each independently selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, and substituted or unsubstituted heterocycloalkylalkyl; and Y is hydrogen, hydroxy, alkoxy, substituted or unsubstituted amino, substituted thio, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkylalkyl, or substituted or unsubstituted heterocycloalkylalkyl.

* * * * *